United States Patent [19]

Chernack et al.

[11] 4,259,951

[45] Apr. 7, 1981

[54] DUAL VALVE FOR RESPIRATORY DEVICE

[75] Inventors: Milton P. Chernack, West Hempstead; Mishel Greenberg, New Hyde Park, both of N.Y.

[73] Assignee: Chesebrough-Pond's Inc., Greenwich, Conn.

[21] Appl. No.: 62,162

[22] Filed: Jul. 30, 1979

[51] Int. Cl.³ .................................... A61M 16/00
[52] U.S. Cl. .......................... 128/200.14; 128/200.18; 128/205.24; 128/207.16; 128/725; 137/102; 137/512.15; 137/512.4
[58] Field of Search ............... 128/200.18, 200.21, 128/203.11, 204.26, 205.13, 205.24, 207.12, 207.16, 152, 206.15, 725; 137/512.4, 512.15, 102; 272/99 R

[56] References Cited

U.S. PATENT DOCUMENTS

| | | | |
|---|---|---|---|
| 2,669,979 | 2/1954 | Kiekhaefer | 137/512.4 X |
| 3,519,012 | 7/1970 | Van Patten | 137/512.15 X |
| 3,527,242 | 9/1970 | Ansite | 137/512.4 X |
| 4,182,347 | 1/1980 | Russo | 128/725 |

FOREIGN PATENT DOCUMENTS 2915683 10/1979 Fed. Rep. of Germany ...... 128/205.24
2019223 10/1979 United Kingdom ............... 128/200.21

*Primary Examiner*—Henry J. Recla

[57] ABSTRACT

A dual valve for an inhalation device which permits air to be withdrawn from the device upon inhalation but which prevents the flow of air into the device upon exhalation. The valve includes a central opening in communication with the device, and a plurality of openings about the central opening in communication with the surrounding environment. The valve also includes a central flexible flapper valve which extends across and controls the flow of air through the central opening, and a plurality of outer flexible flapper valves which extend across and control the flow of air through the outer openings.

In use, inhalation by a user opens the central flexible flapper valve to allow the free flow of air from the inhalation device while the outer flapper valves remain closed. Correspondingly, exhalation by the user opens the outer flexible flapper valves from their seats to exhaust air to the surrounding atmosphere while the central flexible valve remains closed.

7 Claims, 7 Drawing Figures

4,259,951

DUAL VALVE FOR RESPIRATORY DEVICE

FIELD OF THE INVENTION

This invention relates to a dual valve for controlling the flow of air for an incentive inhalation device.

BACKGROUND OF THE INVENTION

U.S. Pat. Nos. 4,060,074, 4,086,918, 4,114,607 and 4,114,608 of Cheseborough Pond's Inc. disclose inhalation devices which provide simple, safe, inexpensive means for inducing a patient to expand his or her lungs and exercise his or her respiratory musculature. These devices include one or more see-through chambers having a light weight article in each chamber, and means, such as flexible tubing and a mouthpiece, to allow a person to withdraw air from the device and to cause the articles therein to rise when the predetermined inhalation effort is achieved. In doing so, the rise and fall of the light weight articles provides the user with an incentive to exercise his or her respiratory system.

When the user exhales air from his or her lungs, however, such air can flow into the inhalation device via the mouthpiece and flexible tubing. This exhaled air contains higher levels of carbon dioxide and normally is ladened with water vapor. Upon repeated inhalation and exhalation the amount of carbon dioxide inspired increases while the amount of oxygen decreases. This effect is not desirable. At the same time the water vapor of the exhaled air can cause condensation within the chambers of the inhalation device. This condensation is undesirable because it may contain detrimental bacteria which may be inspired back into the lungs of the user, and because it clouds and obstructs the view of the light weight articles within the chambers.

Although these problems may be obviated by instructing the user to remove his or her mouth from the device upon exhalation, with weak, feeble or very ill patients, that may be more difficult than would appear. These users often are somewhat uncoordinated and disoriented and may not be fully able to follow such instructions.

It is the object of the invention, therefore, to prevent exhaled air from flowing into the inhalation device without requiring the user to remove his or her mouth from the mouthpiece.

It is another object of this invention to provide a dual valve for an inhalation device which freely permits air to be withdrawn from the device upon inhalation while preventing the flow of air into the device upon exhalation.

Additional objects and advantages will be set forth in part hereinafter and in part will be obvious herefrom or may be learned with the practice of the invention, the same being realized and obtained by means of this dual valve recited in the appended claims.

SUMMARY OF THE INVENTION

In accordance with the invention, there is provided a dual valve for an inhalation device which permits a user to withdraw air from the device upon inhalation and which prevents the flow of air into the device upon exhalation by such user. The valve includes a disk having a central opening in communication with the device, valve seat means operatively connected to said central opening, and a plurality of openings about the central opening in communication with the surrounding environment. Juxtaposed to this disk is another disk having a central opening in communication with the means, such as a mouthpiece, which is used for inhalation and exhalation by the user, a plurality of openings about this central opening also in communication with the mouthpiece, and a plurality of valve seats operatively connected to these outer openings. Further, these disks are positioned relative to one another so that the central and outer openings are in axial alignment. Intermediate the disks, and in contact therewith, is a flexible disk having a central, flexible flapper valve which extends across and controls the flow of air through said central openings, and a plurality of outer flexible flapper valves which extend across and control the flow of air through said outer openings.

Preferably, the dual valve is connected between the mouthpiece and outlet of the inhalation device. In use, inhalation by the user urges the central flexible flapper valve from its seat to open and allow communication between the central openings of the disks and thereby permit the free flow of air from the inhalation device, while the outer flapper valves prevent communication between the outer openings by remaining closed on their seats. Correspondingly, exhalation by the user urges the outer flexible flapper valves from their seats to open and allow communication between the outer openings to exhaust air to the surrounding atmosphere, while the central flexible flapper prevents communication between the central openings by remaining closed on its seat. In doing so, the undesirable exhaled air is prevented from flowing into the inhalation device.

Moreover, the dual valve of the present invention preferably includes dampening means connected thereto adapted to prevent the flexible disk with its central flexible flapper valve from producing noise producing vibrations upon use thereof.

Thus, the dual valve of the present invention prevents the exhalation of air from flowing into an inhalation device without disrupting the normal function and operation of the device.

BRIEF DESCRIPTION OF THE DRAWINGS

The following is a detailed description together with accompanying drawings of a preferred embodiment of the invention. It is to be understood that the invention is capable of modification and variation apparent to those skilled in the art within the spirit and scope of the invention.

In the drawings:

FIG. 2A is a perspective view of the upstream connector of the dual valve which includes the preferred dampening means of the invention.

Figure 1:
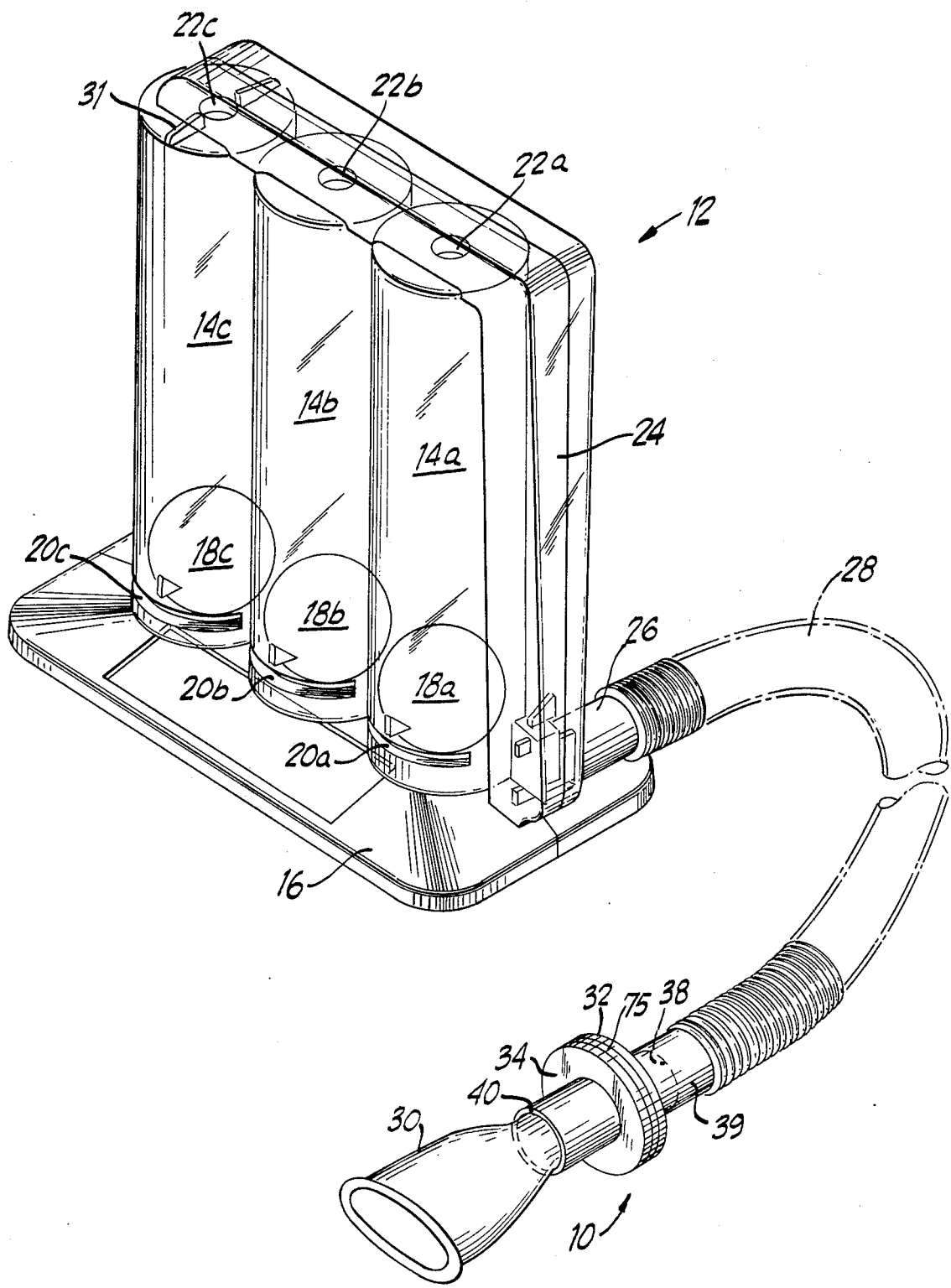
FIG. 1 is a perspective view of an inhalation device wherein the dual valve of the present invention has been included between the mouthpiece and flexible tubing of such device.
Figure 2:
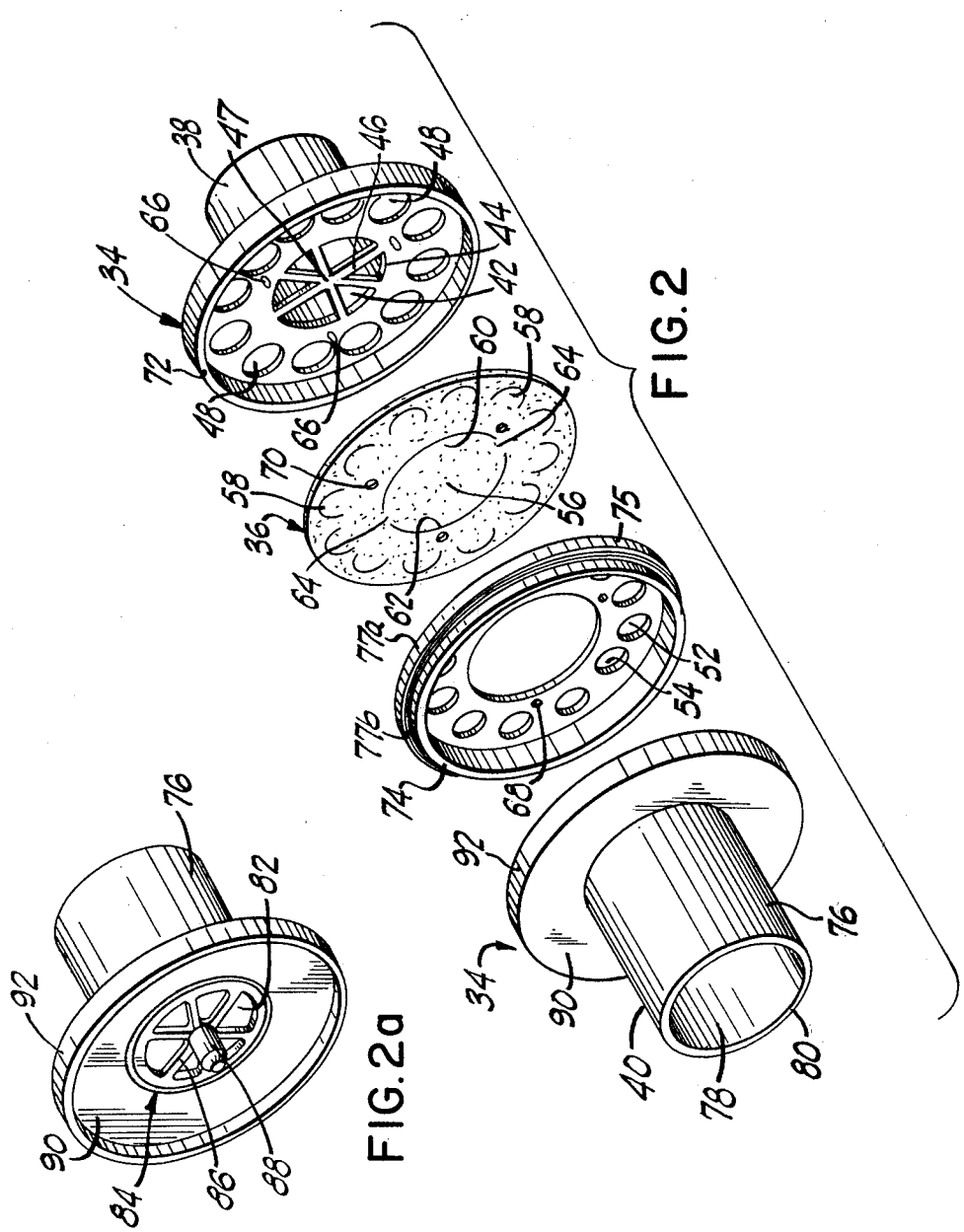
FIG. 2 is an exploded, perspective view of the dual valve of the present invention.

Referring to the drawings and first to FIG. 1, there is shown a preferred embodiment of the dual valve 10 of the invention with an illustrative embodiment of the multi-chambered inhalation device 12 of U.S. Pat. No. 4,060,074.

Generally, the device 12 has three see-through chambers, 14a, 14b and 14c, mounted on a base 16. Within the chambers 14a–14c, are flow rate indicators, such as the plastic balls 18a, 18b and 18c. Extending through and across the lower portion of the chambers 14a–14c are slots 20a, 20b and 20c which connect the lower portions of the chambers 14a–14c to the surrounding atmosphere. Extending through the top of the chambers 14a–14c are ports 22a, 22b and 22c. Extending over the top of the chambers 14a–14c and alongside of the chamber 14a is a passageway 24 which is open to the ports 22a–22c and to an outlet 26 at the base 16. Connected to the outlet 26 is flexible tubing 28, and connected to such tubing 28, through the dual valve 10, is a mouthpiece 30.

In operation, the patient or user places his or her mouth over the mouthpiece 30 and inhales. This action causes air to be withdrawn from and into the chambers 14a–14c via the passageway 24 and slots 20a–c. When the inhalation effort reaches a precalibrated rate, the incoming air will lift the ball 18a to the top of the chamber 14a where it closes the port 22a. Sustained inhalation effort at the precalibrated rate then will cause the intermediate ball 18b to rise to the top of the chamber 14b where it closes the port 22b. Finally, the ball 18c in chamber 14a will rise to the top thereof when the inhalation effort is maintained at the precalibrated rate. In the chamber 14c, however, a depending ridge 31 prevents the ball 18c from closing port 22c and abruptly disrupting the air flow.

As long as the user continues to expend a sufficient inhalation effort, the balls 18a–c will remain at the top of the chambers 14a–c. When the user begins to exhale the balls 18a–c will drop.

For a more detailed description of the structure and operation of the illustrated inhalation device, as well as other typical inhalation devices for which the dual valve 10 of the present invention is useful, reference can be made to the identified Chesebrough patents. It is to be understood, moreover, that the dual valve 10 of the present invention is not limited to the inhalation devices of these patents. The valve 10 also can be used from other inhalation devices where it is desirable to prevent the flow of air thereinto upon exhalation of the user or patient.

Referring now to FIGS. 2–5, the dual valve 10 of the present invention includes a pair of juxtaposed rigid disks 32 and 34 having openings for the passage of air therethrough, an intermediate flexible disk 36 having flapper valves for opening and closing the openings of the disks 32 and 34, and connectors 38 and 40 for connecting the valve 10 to the flexible tubing 28 and mouthpiece 30, respectively.

The disk 32 is on the side of the valve 10 closest to the inhalation device 10, and includes a large central opening 42 which is in communication with the device 10 through the connector 38 and flexible tubing 28. Extending across the central opening 42 is a valve seat 44 which includes the periphery about the opening itself and supporting ribs 46 extending from the center of the opening 42 to the periphery thereof. As shown, there are six equi-spaced radial ribs 46 radiating outwardly from a central portion 47. About the central opening 42 there are a plurality of smaller openings 48 extending through the disk 32. As shown, there are twelve equi-spaced outer openings 48 in communication with the surrounding atmosphere.

In this embodiment of the invention the connector 38 is a sleeve which extends from the disk 32 about the opening 42. The sleeve 38 can be tapered for receipt of an adaptor 39 of the flexible tubing 28 and, as shown, slidably fits thereover (or outside the valve fitment) to secure the tubing 28 to the dual valve 10.

The disk 34 is positioned on the side of the valve 10 closest to the mouthpiece 30, and includes a large central opening 50 adapted to be in communication with the mouth of the user through the connector 40 and mouthpiece 30. About the central opening 50 there are smaller openings 52. In this illustrative embodiment, there are twelve equi-spaced outer openings 52, and the periphery about these openings 52 form valve seats 54 (see FIGS. 3–5). To provide such seats 54 the breadth of the openings 52 is less than the breadth of the openings 48 in the other outer disk 32. Similarly, to form the central valve seat 44 the breadth of the central opening 42 is less than the breadth of the opening 50.

The intermediate disk 36 is flexible and includes a central flexible flapper valve 56 for the central openings 42 and 50 and a plurality of flapper valves 58 for the outer openings 48 and 52.

Figure 3:
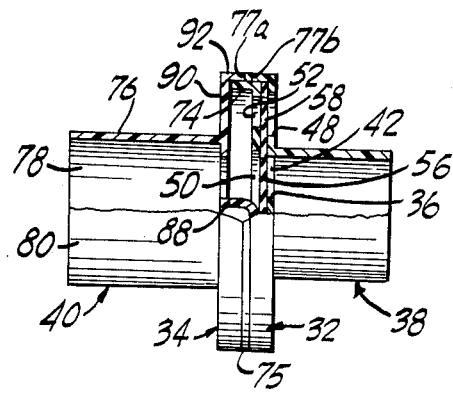
FIG. 3 is a side view, partly in section, of the assembled dual valve of the present invention.

The central flapper valve 56 extends across the openings 42 and 50, and includes two semi-circular segments or flaps 60 and 62 hinged at midpoints 64 to the disk 36. As shown in FIG. 3, these flaps 60 and 62 normally are closed and maintained on their seat 44. To effect such seating the breadth of the flapper valve 56 is greater than the breadth of the opening 42. To allow the valve 56 to open, however, its breadth is less than the breadth of the opening 50.

The outer flapper valves 58 extend across the outer openings 48 and 52. Each valve 58 is in the form of a semi-circular flap hinged at its base to the disk 36. As shown in FIG. 3, these flap valves 58 normally are closed and maintained on their seats 54. In this instance the breadth of the flapper valves 58 is greater than the breadth of the openings 52. Here, to allow the valves 58 to open, their breadth is less than the breadth of the openings 48.

To properly align the disks 32, 34 and 36, the disk 32 includes fingers 66 extending inwardly therefrom and the disks 34 and 36 include corresponding holes 68 and 70. In the illustrative embodiment, there are three equi-spaced fingers 66 and holes 68 and 70 spaced about the central openings 42 and 50 and the flapper valve 56. In the assembled position, fingers 66 extend through the holes 68 and 70 and the intermediate disk 36 is between and contact with the outer disks 32 and 34. With disks 32, 34 and 36 assembled, the central openings 42 and 50 and the central flapper valve 56 are in axial alignment, while the outer openings 48 and 52 and outer flapper valves 58 are similarly aligned.

To maintain the disks 32, 34 and 36 in the assembled and aligned position, the outer disks 32 and 34 include flanges 72 and 74, and the flange 74 includes an annular rib 75 with opposing annular beads 77a and 77b. Both flanges 72 and 74 extend in the same direction, which in the illustrative embodiment is toward the connector 40, and the flange 72 extends over the intermediate disk 36 and slidably fits on the flange 74 until it contacts the bead 77a. To provide this slidable fit the breadth of the disk 34 is slightly less than the breadth of the disk 32.

With respect to the connector 40, it includes a cylindrical tube 76 having an opening 78 therethrough with its outer end 80 adapted to receive the mouthpiece 30 (or nebulizer connection) and with its inner end 82 adapted to have the dampening means 84 connected thereto.

Figure 4:
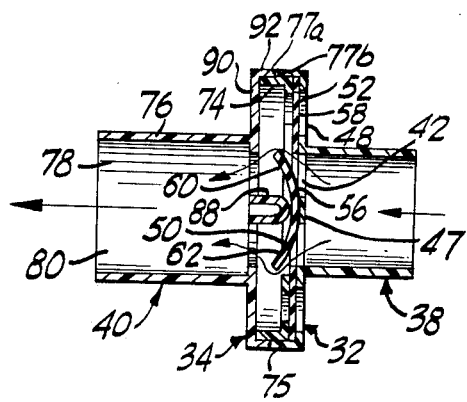
FIG. 4 is a side view, in section of the dual valve of the present invention illustrating the flow of air through the valve upon inhalation.

The dampening means 84 includes supporting ribs 86 extending from the center to the periphery of the inner end 82, and a rod 88 which extends outwardly from the center thereof. As shown in FIGS. 2A and 4 there are six equi-spaced ribs 86 radiating outwardly from the dampening rod 88 which is adapted to extend through the opening 50 of the disk 34 and into contact with the seated central portion of the flapper valve 56 to prevent sound producing vibrations by such valve 56 upon inhalation by a user.

Extending outwardly from the inner end 82 of the tube 76 is an annular plate 90 and a flange 92 adapted to slidably fit over the flange 74 of the disk 34 until it contacts the bead 77b.

With the connector 40 so assembled to the previously described assembled disks 32, 34 and 36, the various elements of the valve 10 are in their desired relative positions, and can be welded by ultrasonically welding the beads 77a and 77b on the annular rib 75 to the flanges 72 and 92.

When ready for use, the mouthpiece 30 slidably engages the valve connector 40 and the tubing 28 slidably engages the valve connector 38. In use, a person places his or her mouth over the mouthpiece 30 and inhales. Upon inhalation, air passes from the device 12 through the flexible tubing 28, into and through the dual valve 10. As specifically illustrated in FIG. 4, inhalation causes the segments 60 and 62 of the flapper valve 56 to flex in the direction of inhalation (toward the mouthpiece 30) with the dampening rod 88 contacting the central portion of the valve 56 to keep it on or adjacent to the central portion 47 of the seat 44. This causes the flapper valve 56 to open the openings 42 and 50 without noise producing vibrations. Continued inhalation causes air to flow from the inhalation device, through the flexible tubing 28 into and through the valve 10, via, the central openings 42 and 50, and finally into the mouthpiece 30 and the lungs of the user. As we have previously described, when this inhalation effort reaches a precalibrated rate of flow, the balls 18a-c in the chambers 14a-c will sequentially rise. As also shown in FIG. 4 during inhalation, the outer valves 58 remain closed on their seats 54 preventing the flow of air through the outer openings 48 and 52.

Figure 5:
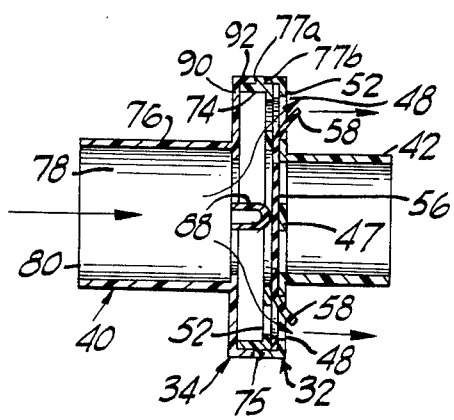
FIG. 5 is a side view illustrating exhausting air from the dual valve to the surrounding atmosphere to prevent the formation of condensation within an inhalation device upon exhalation.

Upon completion of the inhalation effort, the user will begin to exhale through the mouthpiece 30. As illustrated in FIG. 5, such air will impinge upon the central valve 56 which remains closed and on its seat 44. Consequently, the air will flow outwardly within the valve 10 and impinge upon the outer flap valves 58 causing them to flex and open by extending into and through the outer openings 48 in the disk 34. As this occurs, exhalation air is exhausted through the openings 48 and 52 to the surrounding atmosphere. In doing so, exhalation air does not flow into the device 12. There is no carbon dioxide or exccessive water vapor build up in the device 12.

Thus, by the practice of this invention there is provided a dual valve which freely permits the proper use of the inhalation device without requiring the user to remove his or her mouth upon exhalation.

The dual valve 10 of the present invention, moreover, can be used with a medicinal dispenser to dispense medicine while the user exercises his or her lungs and musculature with inhalation devices, such as those disclosed in U.S. Pat. Nos. 4,060,074, 4,086,918, 4,114,607 and 4,114,608 of Chesebrough-Pond's Inc. Illustrative of such dispensers are the nebulizers disclosed in U.S. Pat. No. 4,114,607, which disclosure is incorporated herein by reference.

Figure 6:
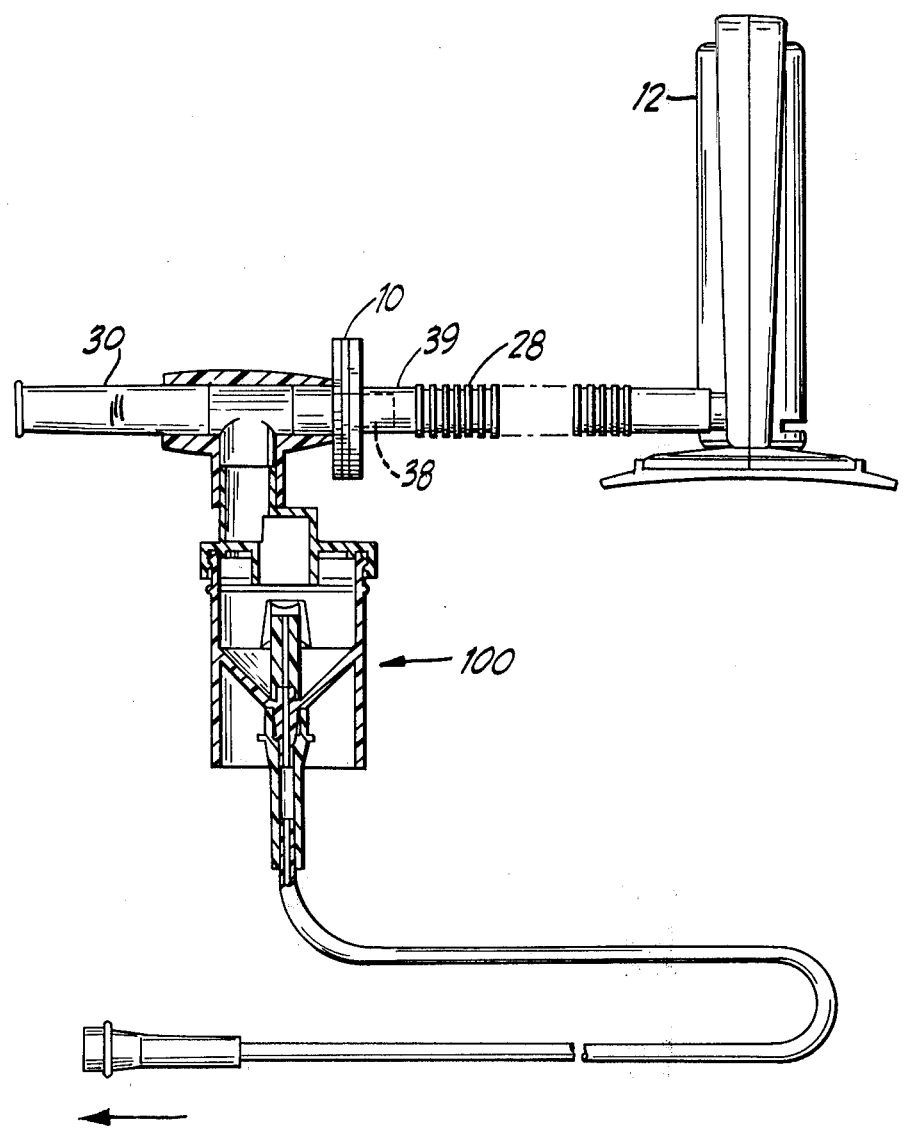
FIG. 6 is a side view of the inhalation device and dual valve of FIG. 1 in which a nebulizer is shown between the mouthpiece and dual valve.

In FIG. 6 of this application the nebulizer 100 of U.S. Pat. No. 4,114,607 is connected to the valve 10 and the flexible tubing 28. As shown, the valve 10 is positioned between the inhalation device 12 and the nebulizer 100. With the nebulizer 100 appropriately connected to a gas source, inhalation by a user, as has been described, will cause medicine in the nebulizer 100 to be inhaled as the user exercises. As also previously described upon exhalation, the expired air will flow through the valve 10 to atmosphere without flowing into the inhalation device 12.

The invention in its broader aspect is not limited to the specific described embodiments and departures may be made therefrom within the scope of the accompanying claims without departing from the principals of the invention and without sacrificing its chief advantages.

What we claim:

1. A dual valve for an inhalation device which permits air to be withdrawn from the device upon inhalation but which prevents the flow of air into the device upon exhalation, comprising:

a first disk having a central opening adapted to be in communication with the device, valve seat means operatively connected to the periphery of said central opening, and a plurality of openings about said central opening in communication with the surrounding environment, a second disk having a central opening adapted to be in communication with means for allowing inhalation and exhalation, a plurality of openings about said central opening also adapted to be in communication with said means, and a plurality of valve seats operatively connected to the periphery of each of said outer openings, said first and second disks being juxtaposed to one another with said central openings and outer openings in axial alignment, an intermediate flexible disk between and in contact with said first and second disks including a central, flexible flapper valve which extends across said central openings and seats on said valve seat means to control the flow of air therethrough, and a plurality of outer flexible flapper valves which extend across said outer openings and seat on said plurality of valve seats, respectively, to control the flow of air therethrough, said central opening in said second disk being of a size to allow said central, flexible flapper valve to pass therethrough and each of said plurality of openings on said first disk being of a size to allow said outer flexible flapper valves to pass therethrough, wherein said central flexible valve is urged from said central valve seat to open said central openings upon inhalation to allow the flow of air from the inhalation device while said outer flexible flapper valves close said outer openings, and wherein said outer flexible flapper valves are urged from their seats to open said outer openings upon exhalation to exhaust air to the surrounding atmosphere while said central flexible flapper valve closes said central openings and prevents the flow of air into the inhalation device.

2. The dual valve of claim 1, wherein said first and second disks have outer flanges which extend in the same direction, and wherein the flange of said first disk slidably fits over said intermediate flexible disk and said second disk to maintain said disks in assembly, and wherein said first disk has an annular rib thereabout with a bead which is in contact with said first disk adapted to secure said assembly together by ultrasonic welding.

3. The dual valve of claim 1, wherein said intermediate flapper valve has two flexible semi-circular segments hinged at their midpoints to said flexible disk, and wherein said segments flex in the direction of said means to open said central openings upon inhalation.

4. The dual valve of claim 3, wherein said valve includes dampening means connected thereto which are adapted to contact the central portion of said intermediate flapper valve to inhibit noise producing valve vibrations upon flexing of said intermediate flapper valve segments.

5. The dual valve of claim 3 wherein said outer flapper valves are flexible semi-circular flaps hinged at their bases to said flexible disks, and wherein said flaps flex to open said outer openings in the direction of said outer openings of said disk in communicatin with said device.

6. In an inhalation device having an outlet tubing having one end connected to the outlet of the device and a mouthpiece connected to the other end of said tubing, a dual valve for inhalation and exhalation connected in said tubing which permits air to be withdrawn from the device upon inhalation but which prevents the flow of air into the device upon exhalation, comprising:

one disk having a central opening in communication with said tubing and said device, valve seat means operatively connected to the periphery of said central opening, and a plurality of openings about said central opening in communication with the surrounding environment, another disk having a central opening in communication with said tubing and said mouthpiece, a plurality of openings about said central opening in communication with said tubing and said mouthpiece, and a plurality of valve seats operatively connected to the periphery of each of said outer openings, said disks being juxtaposed to one another with said central openings and outer openings in axial alignment, a flexible disk between and in contact with said disks including a central, flexible flapper valve which extends across said central openings and seats on said valve seat means to control the flow of air therethrough, and a plurality of outer flexible flapper valves which extend across said outer openings and seat on said plurality of valve seats, respectively, to control of flow of air therethrough, said central opening in said another disk being of a size to allow said central flexible flapper valve to pass therethrough and each of said one disk being of a size to allow said outer flexible flapper valves to pass therethrough, connecting means for connecting said disks between the tubing and mouthpiece with said one disk in communication with the device through the tubing and with said another disk in communication with said mouthpiece, wherein said central flexible valve is urged from said central valve seat to open said central openings upon inhalation to allow the flow of air from the inhalation device while said outer flexible flapper valves close said outer openings, and wherein said outer flexible flapper valves are urged from their seats to open said outer openings upon exhalation to exhaust air to the surrounding atmosphere upon exhalation while said central flexible flapper valve closes said central openings and prevents the flow of air into the inhalation device, to thereby inhibit excessive carbon dioxide and water vapor build up therewithin.

7. In the inhalation device of claim 6, a medicinal dispenser connected in said tubing between said dual valve and said device, wherein said dual valve allows medicine in said dispenser to be withdrawn therefrom into the lungs of a user upon inhalation by such user through said mouthpiece, while preventing air exhaled through the mouthpiece by the user from flowing into the device.

* * * * *